United States Patent [19]

Moreau et al.

[11] Patent Number: 5,811,587
[45] Date of Patent: Sep. 22, 1998

[54] PROCESS FOR THE HYDROXYALKYLATION OF A CARBOCYCLIC AROMATIC ETHER

[75] Inventors: Claude Moreau, Laverune; Sylvie Razigade-Trousselier, Castelnau le Lez; Annie Finiels, Montpellierf; Francois Fajula, Teyran; Laurent Gilbert, Paris, all of France

[73] Assignee: Rhone-Poulenc Chimie, Courbevoie, France

[21] Appl. No.: 776,495

[22] PCT Filed: May 24, 1996

[86] PCT No.: PCT/FR96/00778

§ 371 Date: Jan. 23, 1997

§ 102(e) Date: Jan. 23, 1997

[87] PCT Pub. No.: WO96/37452

PCT Pub. Date: Nov. 28, 1996

[30] Foreign Application Priority Data

May 24, 1995 [FR] France .................................. 95 06187

[51] Int. Cl.⁶ .................................................. C07C 45/36
[52] U.S. Cl. ........................... 568/432; 568/764; 568/771
[58] Field of Search ..................... 568/432, 764, 568/771

[56] References Cited

U.S. PATENT DOCUMENTS

| 3,496,239 | 2/1970 | Hamilton | 260/619 |
|---|---|---|---|
| 3,673,257 | 6/1972 | Di Bella | 260/600 |
| 4,026,950 | 5/1977 | Le Ludec | 260/600 |
| 4,119,671 | 10/1978 | Bauer | 260/600 |
| 4,351,962 | 9/1982 | Gradeff et al. | 568/432 |
| 4,366,325 | 12/1982 | Wedemeyer et al. | 568/432 |
| 5,003,114 | 3/1991 | Costantini et al. | 568/771 |
| 5,254,746 | 10/1993 | Costantini et al. | 568/626 |

FOREIGN PATENT DOCUMENTS

| 0 485 613 | 5/1992 | European Pat. Off. | C07C 39/11 |
|---|---|---|---|
| 0 667 331 | 8/1995 | European Pat. Off. | C07C 45/38 |
| 80 59128 | 5/1980 | Japan | C07C 47/575 |

OTHER PUBLICATIONS

Studies in Surface Science and Catalysis, vol. 78, 1993, pp. 567–574, XP002023490 M. H. Burgers et al: "Aromatic hydroxyalkylation using (silico) aluminophosphate molecular sieves" (see tables 1–3).

*Primary Examiner*—Gary Geist
*Assistant Examiner*—Sreeni Padmanabhan
*Attorney, Agent, or Firm*—Katherine L. Carleton; John A. Shedden; Jean-Louis Seugnet

[57] ABSTRACT

The present invention concerns a process for the hydroxyalkylation of a carbocyclic aromatic ether.

The invention preferably relates to the preparation of 3-methoxy-4-hydroxybenzyl alcohol by the hydroxymethylation of guaiacol.

It also concerns the oxidation of the hydroxyalkylated ethers obtained, in particular the oxidation of 3-methoxy-4-hydroxybenzyl alcohol to 3-methoxy-4-hydroxybenzaldehyde, commonly known as "vanillin".

The process for the hydroxyalkylation of a carbocyclic aromatic ether of the invention consists of reacting the aromatic ether with a carbonyl compound in the presence of a catalyst and is characterized in that the hydroxyalkylation reaction is carried out in the presence of an effective quantity of a zeolite.

39 Claims, No Drawings

PROCESS FOR THE HYDROXYALKYLATION OF A CARBOCYCLIC AROMATIC ETHER

This is the US National Stage Application of PCT/FR96/00778 filed May 24, 1996 now WO96/37452 published Nov. 28, 1996.

The present invention concerns a process for the hydroxyalkylation of a carbocyclic aromatic ether.

The invention preferably relates to the preparation of 3-methoxy-4-hydroxybenzyl alcohol, known as "p-vanillol", by the hydroxymethylation of guaiacol.

It also concerns the oxidation of the hydroxyalkylated ethers obtained, in particular the oxidation of 3-methoxy-4-hydroxybenzyl alcohol to 3-methoxy-4-hydroxybenzaldehyde, commonly known as "vanillin".

European patent EP-A-0 485 613 describes the para-hydroxymethylation of a phenol, in particular guaiacol, by reacting the latter with formaldehyde in an alcoholic organic solvent and in the presence of a quaternary ammonium compound such as tetramethylammonium hydroxide.

In addition to having to work in an anhydrous alcoholic medium, the major disadvantage of that process is the use of a quaternary ammonium compound which must be recovered at the end of the reaction as it is expensive.

The present invention provides a novel process which uses a heterogeneous catalyst which can overcome the above disadvantages.

We have now discovered, and this forms an object of the present invention, a process for the hydroxyalkylation of a carbocyclic aromatic ether which consists of reacting the aromatic ether with a carbonyl compound in the presence of a catalyst, characterized in that the hydroxyalkylation reaction is carried out in the presence of an effective quantity of a zeolite.

The invention concerns carbocyclic aromatic ethers.

In the following disclosure of the invention, the term "carbocyclic aromatic ether" denotes an aromatic carbocycle in which one hydrogen atoms which is directly bonded to the aromatic nucleus is replaced by an ether group, and the term "aromatic" denotes the conventional concept of aromaticity as defined in the literature, in particular by Jerry MARCH, Advanced Organic Chemistry, 4th edition, John Wiley and Sons, 1992, pp. 40 ff.

More precisely, an object of the present invention is to provide a process for the hydroxyalkylation of a carbocyclic aromatic ether with general formula (I):

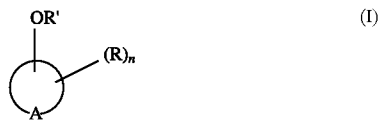

where:
A represents the residue of a cycle forming all or a portion of a monocyclic or polycyclic aromatic carbocyclic system containing at least one OR' group: the cyclic residue may carry one or more substituents;
R represents one or more substituents which may be identical or different;
R' represents a hydrocarbon radical containing 1 to 24 carbon atoms, which may be a saturated or unsaturated, linear or branched acyclic aliphatic radical; a monocyclic or polycyclic, and saturated, unsaturated or aromatic cycloaliphatic radical; or a saturated or unsaturated, linear or branched aliphatic radical carrying a cyclic substituent;
R' and R may form a cycle which may contain a further heteroatom;
n is a number less than or equal to 4.

For simplicity in the present text, the term "alkoxy groups" denotes —O—R' type groups where R' has the meaning given above. R' thus represents both a saturated, unsaturated or aromatic, acyclic or cycloaliphatic aliphatic radical and a saturated or unsaturated aliphatic radical carrying a cyclic substituent.

The carbocyclic aromatic ether used in the process of the invention has formula (I) where R' represents a saturated or unsaturated, linear or branched acyclic aliphatic radical.

More preferably, R' represents a linear or branched alkyl radical containing 1 to 12 carbon atoms, preferably 1 to 6 carbon atoms: the hydrocarbon chain may be interrupted by a heteroatom (for example oxygen), by a functional group (for example —CO—) and/or may carry a substituent (for example a halogen).

The saturated or unsaturated, linear or branched acyclic aliphatic radical may carry a cyclic substituent. The term cycle preferably denotes a saturated, unsaturated or aromatic carbocyclic cycle, preferably cycloaliphatic or aromatic, and in particular cycloaliphatic containing 6 carbon atoms in the cycle, or benzenic.

The acyclic aliphatic radical may be bonded to the cycle by a valence bond, a heteroatom or a functional group; examples are given above.

The cycle may optionally be substituted; examples of cyclic substituents are substituents such as R whose meaning is described for formula (Ia).

R' may also represent a carbocyclic radical which is saturated or contains 1 or 2 unsaturations in the cycle, generally containing 3 to 8 carbon atoms, preferably 6 carbon atoms in the cycle; the cycle may be substituted with substituents such as R.

R' may also represent an aromatic carbocyclic radical, preferably a monocyclic radical generally containing at least 4 carbon atoms, preferably 6 carbon atoms in the cycle; the cycle may be substituted with substituents such as R.

The process of the invention is particularly applicable to aromatic ethers with formula (I) where R' represents a linear or branched alkyl radical containing 1 to 4 carbon atoms or a phenyl radical.

Examples of preferred radicals R' of the invention are methyl and ethyl.

In general formula (I) for aromatic ethers, residue A may represent the residue of a monocyclic aromatic carbocyclic compound containing at least 4 carbon atoms, preferably 6 carbon atoms, or the residue of a polycyclic carbocyclic compound which may be constituted by at least 2 aromatic carbocycles and form between them ortho- or ortho- and pericondensed systems or by at least 2 carbocycles of which at least one is aromatic and forming between them ortho- or ortho- and pericondensed systems. A particular example is a naphthalenic residue.

Residue A may carry one or more substituents on the aromatic nucleus.

Examples of substituents R are given below in formula (Ia), but this list is not limiting. Any substituent can be present on the cycle provided that it does not interfere with production of the desired product.

The process of the invention is particularly applicable to aromatic ethers with formula (Ia):

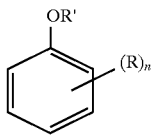

where:
n is a number less than or equal to 4, preferably 0, 1 or 2;
radical R' represents a linear or branched alkyl radical containing 1 to 6 carbon atoms, preferably 1 to 4 carbon atoms, such as methyl, ethyl, propyl, isopropyl, butyl, isobutyl, sec-butyl, tert-butyl or a phenyl radical;
radical(s) R represent one of the following atoms or groups:
- a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
- a linear or branched alkenyl radical containing 2 to 6 carbon atoms, preferably 2 to 4 carbon atoms, such as vinyl, allyl;
- a cyclohexyl or benzyl radical;
- a linear or branched alkoxy radical containing 1 to 6 carbon atoms, preferably 1 to 4 carbon atoms, such as a methoxy, ethoxy, propoxy, isopropoxy or butoxy radical;
- an acyl group containing 2 to 6 carbon atoms;
- a radical with formula:
    —$R_1$—OH
    —$R_1$—$COOR_2$
    —$R_1$—CHO
    —$R_1$—$NO_2$
    —$R_1$—CN
    —$R_1$—N—$(R_2)_2$
    —$R_1$—CO—N—$(R_2)_2$
    —$R_1$—X
    —$R_1$—$CF_3$
    where $R_1$ represents a valence bond or a, saturated or unsaturated, linear or branched divalent hydrocarbon radical containing 1 to 6 carbon atoms such as methylene, ethylene, propylene, isopropylene, or isopropylidene; radicals $R_2$, which may be identical or different, represent a hydrogen atom or a linear or branched alkyl radical containing 1 to 6 carbon atoms; and X represents a halogen atom, preferably a chlorine, bromine or fluorine atom;

radicals R' and R and the 2 successive atoms of the benzene ring may form between them a cycle containing 5 to 7 carbon atoms, which may contain a further heteroatom.

When n is greater than or equal to 1, radicals R' and R and the 2 successive atoms of the benzene ring can be bonded together by an alkylene, alkenylene or alkenylidene radical containing 2 to 4 carbon atoms to form a saturated, unsaturated or aromatic heterocycle containing 5 to 7 carbon atoms. One or more carbon atoms may be replaced by a further heteroatom, preferably oxygen. Thus radicals OR' and R may represent a dioxymethylene or a dioxyethylene radical.

In formula (Ia), R' preferably represents a linear or branched alkyl radical containing 1 to 4 carbon atoms, preferably a methyl or ethyl radical.

The aromatic ether with formula (I) may carry one or more R substituents.

More preferably, R represents one of the following atoms or groups:
- a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
- a linear or branched alkoxy radical containing 1 to 6 carbon atoms, preferably 1 to 4 carbon atoms, such as a methoxy, ethoxy, propoxy, isopropoxy, butoxy, isobutoxy, sec-butoxy or tert-butoxy radical;
- a halogen atom, preferably a fluorine, chlorine or bromine atom, or a trifluoromethyl radical.

In formula (Ia), R preferably represents a linear or branched alkoxy radical containing 1 to 4 carbon atoms, preferably a methoxy or ethoxy radical, or a hydroxy radical.

Preferably, aromatic ethers with formula (I) or (Ia) are used in which:
n equals 0 or 1;
R' represents a linear or branched alkyl radical containing 1 to 4 carbon atoms or a phenyl radical;
R represents a linear or branched alkoxy radical containing 1 to 4 carbon atoms, preferably a methoxy or ethoxy radical, or a hydroxy radical;
radicals OR' and R form a dioxymethylene or dioxyethylene radical.

The process of the invention is particularly applicable to aromatic ethers with formula (Ia) where n equals 1, radical R' represents an alkyl radical containing 1 to 4 carbon atoms and R represents an alkoxy radical containing 1 to 4 carbon atoms or a hydroxy group.

Particular illustrations of compounds with formula (I) are:
monoethers such as anisole, ethoxybenzene (phenetole), propoxybenzene, isopropoxybenzene, butoxybenzene, isobutoxybenzene, 1-methoxynaphthalene, 2-methoxynaphthalene, 2-ethoxynaphthalene; substituted monoethers such as 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 1-methoxy-2-allyloxybenzene, 2,3-dimethylanisole, and 2,5-dimethylanisole;
diethers such as veratrol, 1,3-dimethoxybenzene, 1,4-dimethoxybenzene, 1,2-diethoxybenzene, 1,3-diethoxybenzene, 1,2-dipropoxybenzene, 1,3-dipropoxybenzene, 1,2-methylenedioxybenzene, and 1,2-ethylenedioxybenzene;
triethers such as 1,2,3-trimethoxybenzene, 1,3,5-trimethoxybenzene and 1,3,5-triethoxybenzene.

Compounds for which the process of the invention is particularly applicable are anisole, phenetole, guaiacol, guetol, veratrol, 1,2-methylenedioxybenzene, and 2-methoxynaphthalene.

More particularly, the carbonyl compound has the following general formula (II):

$$R_3—C(=O)—R_4 \quad (II)$$

where:
$R_3$ and $R_4$, which may be identical or different, represent:
- a hydrogen atom;
- a linear or branched alkyl radical containing 1 to 6 carbon atoms;
- a linear or branched alkenyl group containing 2 to 6 carbon atoms;
- a phenyl group;
- an electron withdrawing group.

In the following disclosure of the present invention, the term "electron withdrawing group" denotes a group as defined by H. C. BROWN in the book by Jerry MARCH, "Advanced Organic Chemistry", Chapter 9, pp. 243 and 244.

Examples of electron withdrawing groups which are suitable for the present invention are:
a —CHO group;
a —COOR$_5$ group where R$_5$ represents a hydrogen atom or a linear or branched alkyl radical containing 1 to 6 carbon atoms;
a —CX$_2$H group where X represents a halogen atom, preferably a chlorine atom;
a —CX$_3$ group where X represents a halogen atom, preferably a chlorine atom.

Examples of carbonyl compounds with formula (II) are:
formaldehyde or a formaldehyde generator such as trioxane or paraformaldehyde used in the form of linear polyformaldehydes of any degree of polymerisation, preferably with 8 to 100 (CH$_2$O) units;
glyoxylic acid;
chloral;
dichloroacetone;
acetaldehyde;
propionaldehyde;
dichloroacetaldehyde;
trichloroacetaldehyde;
methyl pyruvate;
ethyl pyruvate.

Of the above compounds, formaldehyde is preferred.

This reactant is generally used as an aqueous solution with a concentration of less than 50% by weight, preferably in the range 20% to 50% by weight. It may contain a few percent of alcohol, generally methanol in a concentration of less than 5% by weight.

In accordance with the process of the invention, the hydroxyalkylation reaction is carried out in the presence of a catalyst constituted by a zeolite.

The term "zeolite" denotes a crystallised tectosilicate of natural or synthetic origin in which the crystals result from a three-dimensional assembly of tetrahedral units of SiO$_4$ and TO$_4$: T represents a trivalent element such as aluminium, gallium, boron or iron, preferably aluminium.

Aluminosilicate type zeolites are the most common.

The crystalline structure of zeolites contains a system of cavities which are interconnected by channels of well defined diameter known as pores.

Zeolites can have a one-dimensional, two-dimensional or three-dimensional network of channels.

A natural or synthetic zeolite can be used in the process of the invention.

Examples of natural zeolites which can be used are: chabazite, clinoptilolite, erionite, phillipsite, and offretite.

Synthetic zeolites can also be used in the process of the invention.

Examples of synthetic zeolites with a one-dimensional network are ZSM-4 zeolite, L zeolite, ZSM-12 zeolite, ZSM-22 zeolite, ZSM-23 zeolite, and ZSM-48 zeolite.

Particular examples of two-dimensional zeolites which can be used are mordenite and ferrierite.

Particular examples of three-dimensional zeolites are β zeolite, Y zeolite, X zeolite, ZSM-5 zeolite, ZSM-11 zeolite and offretite.

Preferably, synthetic zeolites are used, more particularly zeolites in the following forms:
mazzite with a Si/Al molar ratio of 3.4;
L zeolite with a Si/Al molar ratio of 1.5 to 3.5;
mordenite with a Si/Al molar ratio of 5 to 150, preferably 10 to 100, and more preferably 10 to 25;
ferrierite with a Si/Al molar ratio of 3 to 10;
offretite with a Si/Al molar ratio of 4 to 8.5;
β zeolites with a Si/Al molar ratio of 10 to 100, preferably 12 to 50;
Y zeolites, in particular zeolites obtained after a dealuminising treatment (for example hydrotreatment, washing with hydrochloric acid or treatment with SiCl$_4$), in particular US—Y zeolites with a Si/Al molar ratio of more than 3, preferably in the range 6 to 60;
X or faujasite type zeolite with a Si/Al molar ratio of 0.7 to 1.5;
ZSM-5 zeolites or aluminium silicalite with a Si/Al molar ratio of 10 to 500;
ZSM-11 zeolite with a Si/Al molar ratio of 5 to 30.

Of these zeolites, β zeolites and mordenites are preferably used in the process of the invention.

The zeolites used in the process of the invention are known products which are described in the literature [see The "Atlas of Zeolite Structure Types" by W. M Meier and D. H. Olson, published by the Structure Commission of the International Zeolite Association (1992)].

Commercially available zeolites can be used, or they can be synthesised using processes described in the literature.

Reference can be made to the Atlas cited above, in particular for the preparation of:
L zeolite in accordance with the publication by R. M. Barrer et al., Z. Kristallogr., 128, pp. 352 (1969);
ZSM-12 zeolite from U.S. Pat. No. 3,832,449 and the article by LaPierre et al., Zeolites 5, pp 346 (1985);
ZSM-22 zeolite, from the publication by G. T Kokotailo et al., Zeolites 5, pp. 349 (1985);
ZSM-23 zeolite, from U.S. Pat. No. 4,076,842 and the article by A. C. Rohrman et al., Zeolites 5, pp 352 (1985);
ZSM-48 zeolite from the work by J. L. Schlenker et al., Zeolites 5, pp. 355 (1985);
β zeolite, from U.S. Pat. No. 3,308,069 and the article by P. Caullet et al., Zeolites 12, pp. 240 (1992);
mordenite, from the work by Itabashi et al., Zeolites 6, pp. 30 (1986);
X and Y zeolites, respectively from U.S. Pat. No. 2,882,244 and U.S. Pat. No. 3 130 007;
ZSM-5 zeolite, from U.S. Pat. No. 3,702,886 and the article by V. P. Shiralkar et al., Zeolites 9, pp. 363 (1989);
ZSM-11, from the work by I. D. Harrison et al., Zeolites 7, pp. 21 (1987).

In order to use a zeolite with the desired Si/Al atomic ratio, it may be necessary to carry out a dealuminising treatment.

Methods which are known to the skilled person can be used, non exhaustive examples of which are: calcining in the presence of vapour, calcining in the presence of steam followed by attack with mineral acids (HNO$_3$, HCl . . . ), direct dealuminising using reactants such as silicon tetrachloride (SiCl$_4$), ammonium hexafluorosilicate ((NH$_4$)$_2$SiF$_6$), or ethylenediaminetetracetic acid (EDTA) and its mono- or disodium form. Dealuminising can also be carried out by direct acid attack with solutions of mineral acids such as hydrochloric acid, nitric acid, sulphuric acid or organic acids, in particular acetic acid or oxalic acid.

Any combination of the above dealuminising methods is also possible.

The zeolite constitutes the catalytic phase. It can be used alone or mixed with an inorganic matrix. In this description, the term "catalyst" is used to denote a catalyst formed entirely of zeolite or a mixture with a matrix prepared using techniques which are known to the skilled person.

The matrix can be selected from metal oxides such as aluminium oxides, silicon oxides and/or zirconium oxides, or from clays, in particular kaolin, talc or montmorillonite.

The active phase in the catalyst represents 5% to 100% by weight of the catalyst.

The catalysts can be in different forms in the process of the invention: powder, formed products such as granules (for example extrudates or spherules) or pellets, obtained by extrusion, moulding, compacting or any other known process. Granules or spherules are used industrially as they have the most advantages as regards both efficiency and ease of use.

The zeolite is preferably in its acid form. If necessary, it is treated to render it acidic.

Conventional treatments are used in this respect.

Thus, the alkaline cations can be exchanged by treating the zeolite with liquid ammonia to exchange the alkaline cation with an ammonium ion followed by calcining the exchanged zeolite to thermally decompose the ammonium cation and replace it with an $H^+$ ion.

The quantity of liquid ammonia used is at least equal to the quantity required to exchange all the alkaline cations for $NH_4^+$ ions.

Thus $10^{-5}$ to $5 \times 10^{-3}$ moles of 1 ammonia is used per gram of zeolite.

Exchange of the exchangeable cation with $NH_4^+$ is carried out at a temperature between room temperature and the reflux temperature of the reaction medium. The operation takes several hours and can be repeated.

The zeolite can also be acidified using a conventional acid treatment. It can be effected by adding an acid, in particular hydrochloric acid, sulphuric acid, nitric acid, perchloric acid, phosphoric acid or trifluoromethanesulphonic acid.

In a preferred implementation, the zeolite is acidified by passing a volume in the range 10 ml/g to 100 ml/g of acid with a normality which is in the range 0.1N to 2N per gram of zeolite. Passage can be effected in a single step or, preferably, in several successive steps.

Reaction of the carbocyclic aromatic ether with formula (I) with the carbonyl compound with formula (II) is preferably carried out in an aqueous medium when using formaldehyde. However, it is also possible to carry out the reaction in an inert organic liquid under the selected reaction conditions.

Particular examples of suitable solvents are aliphatic or aromatic hydrocarbons which may or may not be halogenated, aliphatic, cycloaliphatic or aromatic ether-oxides, or polar aprotic solvents.

Particular examples of aliphatic or cycloaliphatic hydrocarbons are paraffins, in particular hexane, heptane, octane, nonane, decane, undecane, dodecane, tetradecane or cyclohexane, and aromatic hydrocarbons, in particular benzene, toluene, xylenes, cumene, and petroleum cuts constituted by a mixture of alkylbenzenes, in particular Solvesso® type cuts.

Particular examples of aliphatic or aromatic halogenated hydrocarbons are perchlorinated hydrocarbons, in particular tetrachloroethylene and hexachloroethane; partially chlorinated hydrocarbons such as dichloromethane, chloroform, 1,2-dichloroethane, 1,1,1 -trichloroethane, 1,1 ,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4-dichlorobenzene, 1,2,4-trichlorobenzene or mixtures of different chlorobenzenes; bromoform, bromoethane or 1,2-dibromoethane; monobromobenzene or mixtures of monobromobenzene with one or more dibromobenzenes; and 1 -bromonaphthalene.

Aliphatic, cycloaliphatic or aromatic ether-oxides can also be used as organic solvents, more particularly diethyl oxide, dipropyl oxide, diisopropyl oxide, dibutyl oxide, methyltertiobutylether, dipentyl oxide, diisopentyl oxide, ethyleneglycol dimethyl ether (1,2-dimethoxyethane), diethyleneglycol dimethylether (1,5-dimethoxy-3-oxapentane); phenyl or benzyl oxide; dioxane, and tetrahydrofuran (THF).

Polar aprotic solvents can be used, such as nitrogen-containing compounds, for example nitromethane, nitroethane, 1-nitropropane, 2-nitropropane or mixtures thereof, nitrobenzene; aliphatic or aromatic nitriles such as acetonitrile, propionitrile, butanenitrile, isobutanenitrile, benzonitrile, phenylacetonitrile; dimethylsulphoxide; and tetramethylenesulphone (sulpholane).

Preferred solvents are dichloromethane, tetrachloromethane, dioxane, diethyl oxide, isopropyl oxide and phenyl oxide.

A mixture of organic solvents can also be used.

The concentration of catalyst used can vary between wide limits. It can be in the range 0.1 to 5 moles per liter of medium, preferably in the range 0.2 to 2 moles per liter.

When the process is carried out batchwise, the catalyst can represent 5% to 80% by weight, preferably 10% to 50%, by weight with respect to the aromatic ether used. When the process is carried out continuously, however, for example by reacting a mixture of aromatic ether and carbonyl compound on a fixed catalyst bed, catalyst/aromatic ether ratios do not make sense and at a given instant, there may be an excess by weight of catalyst with respect to the starting aromatic ether.

The quantity of carbonyl compound with formula (II), expressed in moles of carbonyl compound per mole of aromatic ether with formula (I), can also vary between wide limits. The molar ratio of carbonyl compound with formula (II)/aromatic ether with formula (I) can vary between 1 and 50. The upper limit is not critical but for reasons of economy there is no point in exceeding it.

The preferred range for the ratio is determined depending on the nature of the zeolite. Thus, when using natural or synthetic zeolites such as L, X, Y zeolites, mordenites with a molar ratio Si/Al of 5 to 12, ferrierite and offretite, the molar ratio of carbonyl compound/aromatic ether is preferably 1 to 25. It is advantageously between 8 and 25 for synthetic zeolites such as ZSM-4 zeolite, ZSM-5 zeolite, ZSM-11 zeolite, ZSM-12 zeolite, ZSM-22 zeolite, ZSM-23 zeolite, ZSM-48 zeolite, L zeolite, β zeolite and mordenites with a molar ratio Si/Al of 12 to 150.

The temperature of the hydroxyalkylation reaction is no more than 100° C. For better reaction selectivity, a low temperature Is important. However, for sufficient activity, the temperature is advantageously between 20° C. and 100° C., more preferably between 40° C. and 90° C.

In general, the reaction is carried out at atmospheric pressure but higher pressures of 1 bar to 50 bar, preferably 1 bar to 25 bar can also be used. Autogeneous pressure is used when the reaction temperature is higher than the boiling point of the reactants and/or products.

It is preferable to carry out the reaction in a controlled atmosphere of inert gases such as nitrogen or a noble gas, for example argon.

The-reaction period can vary a great deal. It is normally between 15 minutes and 10 hours, preferably between 30 minutes and 5 hours.

In practice, the process can be carried out batchwise or continuously.

In the first variation, the catalyst, carbonyl compound with formula (II) and any solvent is charged, then the aromatic ether is introduced. In a preferred embodiment, the aromatic ether is introduced gradually, either continuously or in fractions then the reaction mixture is heated to the desired temperature.

In the other variation, the reaction is carried out continuously in a tube reactor comprising the solid catalyst disposed in a fixed bed.

Preferably, the carbocyclic aromatic ether and the acylation agent are separately introduced into the reactor.

They can also be introduced in a solvent as mentioned above.

The residence time for the material stream on the catalytic bed varies, for example, between 15 minutes and 10 hours, preferably between 30 minutes and 5 hours.

At the end of the reaction, a liquid phase is recovered containing the hydroxyalkylated aromatic ether is recovered; recovery is conventional, using different methods.

A first method of separating the hydroxyalkylated aromatic ether consists of extraction in an organic solvent then oxidising the organic phase obtained. This method is preferred over the following method when the carbonyl compound is formaldehyde or a formaldehyde precursors.

Particular examples of suitable solvents are halogenated aliphatic or aromatic hydrocarbons such as chloromethane, dichloromethane, 1,2-dichloroethane, chlorobenzene, dichlorobenzenes, or trichlorobenzenes; esters such as butyl, isopropyl, amyl, or cyclohexyl acetates; and ketones such as acetone, methylethylketone, or methylisobutylketone.

The ratio between the organic phase and the aqueous phase is preferably between 0.5 and 1.0 by volume.

The organic and aqueous phases are separated.

The aqueous phase can be recycled to the reaction.

The organic phase can be directly oxidised.

In another variation, the organic phase is brought into contact with a basic aqueous phase to effect counter-extraction in the aqueous phase, with the product being obtained in its salt form; the latter is then oxidised.

This method is suitable when the hydroxyalkylated aromatic ether obtained also carries a hydroxy group, as is the case, for example, with guaiacol.

The alkaline agent in this respect is generally sodium or potassium hydroxide. The proportion of inorganic base used is in the range 0.5 to 3 moles of sodium or potassium hydroxide with respect to the hydroxyalkylated aromatic ether to be oxidised.

The concentration of the latter in the aqueous alkaline agent solution is preferably such that precipitation is avoided to maintain a homogeneous solution. It is normally in the range 1% to 60% by weight, preferably in the range 2% to 30%.

The aqueous phase obtained then undergoes the oxidation step.

In a further variation, the hydroxyalkylated aromatic ether is separated by distillation or recrystallisation from an appropriate solvent after prior elimination of excess reactants then taking up the product obtained into organic solution to carry out the oxidation step.

A preferred oxidation process in accordance with the invention, constituting a further object of the present invention, consists of oxidising the hydroxyalkylated aromatic ether in the liquid phase using molecular oxygen or a gas containing molecular oxygen in the presence of a catalyst based on a metal M selected from the metals in group 8 of the periodic classification of the elements, optionally comprising, as activators, metals such as cadmium, cerium, bismuth, lead, silver, tellurium or tin.

Further details of these catalysts are provided in U.S. Pat. No. 3,673,257, and French patents FR-A-2 305 420 and FR-A-2 350 323.

Examples of catalysts based on a metal from group 8 are nickel, ruthenium, rhodium, palladium, osmium, iridium, platinum and mixtures thereof.

Preferably, platinum and/or palladium catalysts are used, taken from all available forms such as: platinum black, palladium black, platinum oxide, palladium oxide or the noble metal itself deposited on different supports such as carbon black, calcium carbonate, aluminas or activated silicas or equivalent materials. Catalytic masses based on carbon black are particularly suitable.

The quantity of catalyst used, expressed as the weight of metal M with respect to that of the hydroxyalkylated aromatic ether, can vary from 0.01% to 4%, preferably 0.04% to 2%.

The activator can be selected from all those mentioned in the above patents. Preferably, bismuth, lead and cadmium are used as the free metal or as cations. In the latter case, the associated anion is not critical and all derivatives of these metals can be used. Preferably, bismuth metal or its derivatives is used.

An inorganic or organic bismuth derivative can be used in which the bismuth atom has an oxidation number of more than zero, for example 2, 3, 4 or 5. The residue associated with the bismuth is not critical provided that is satisfies this condition. The activator can be soluble or insoluble in the reaction medium.

Illustrative examples of activators which can be used in the process of the present invention are: bismuth oxides; bismuth hydroxides; salts of inorganic hydracids such as: bismuth chloride, bromide, iodide, sulphide, selenide, or telluride; salts of inorganic oxyacids such as: bismuth sulphite, sulphate, nitrite, nitrate, phosphite, phosphate, pyrophosphate, carbonate, perchlorate, antimonate, arsenate, selenite, selenate; salts of oxyacids derived from transition metals such as: bismuth vanadate, niobate, tantalate, chromate, molybdate, tungstate, or permanganate.

Other suitable compounds are the salts of aliphatic or aromatic organic acids such as: bismuth acetate, propionate, benzoate, salicylate, oxalate, tartrate, lactate, citrate; phenates such as: bismuth gallate and pyrogallate. These salts and phenates can also be bismuthyl salts.

Other inorganic or organic compounds are binary compounds of bismuth with elements such as phosphorous or arsenic; heteropolyacids containing bismuth and salts thereof; also aliphatic and aromatic bismuthines.

Specific examples are:

oxides: BiO; $Bi_2O_3$; $Bi_2O_4$; $Bi_2O_5$;

hydroxides: $Bi(OH)_3$;

salts of inorganic hydracids: bismuth chloride $BiCl_3$; bismuth bromide $BiBr_3$; bismuth iodide $BiI_3$; bismuth sulphide $Bi_2S_3$; bismuth selenide $Bi_2Se_3$; bismuth telluride $Bi_2Te_3$;

salts of inorganic oxyacids: basic bismuth sulphite $Bi_2(SO_3)_3, Bi_2O_3, 5\ H_2O$; neutral bismuth sulphate $Bi_2(SO_4)_3$; bismuthyl sulphate $(BiO)HSO_4$; bismuthyl nitrite $(BiO)NO_2, 0.5H_2O$; neutral bismuth nitrate $Bi(NO_3)_3, 5H_2O$; double nitrate of bismuth and magnesium $2Bi(NO_3)_3, 3Mg(NO_3)_2, 24H_2O$; bismuthyl nitrate $(BiO)NO_3$; bismuth phosphite $Bi_2(PO_3H)_3, 3H_2O$; neutral bismuth phosphate $BiPO_4$; bismuth pyrophosphate $Bi_4(P_2O_7)_3$; bismuthyl carbonate $(BiO)_2CO_3; 0.5H_2O$; neutral bismuth perchlorate $(Bi(ClO_4)_3, 5H_2O$; bismuthyl perchlorate $(BiO)ClO_4$; bismuth antimonate $BiSbO_4$; neutral bismuth arsenate $Bi(AsO_4)_3$; bismuthyl arsenate $(BiO)AsO_4, 5H_2O$; bismuth selenite $Bi_2(SeO_3)_3$;

salts of oxyacids derived from transition metals: bismuth vanadate $BiVO_4$; bismuth niobate $BiNbO_4$; bismuth tantalate $BiTaO_4$; neutral bismuth chromate $Bi_2(CrO_4)$; bismuthyl dichromate $([BiO]_2Cr_2O_7$; acid bismuthyl chromate $H(BiO)CrO_4$; double chromate of bismuthyl and potassium $K(BiO)CrO_4$; bismuth molybdate $Bi_2(MoO_4)_3$; bismuth tungstate $Bi_2(WO_4)_3$; double molybdate of bismuth and sodium $NaBi(MoO_4)_2$; basic bismuth permanganate $Bi_2O_2(OH)MnO_4$;

salts of aliphatic or aromatic organic acids: bismuth acetate $Bi(C_2H_3O_2)_3$; bismuthyl propionate $(BiO)C_3H_5O_2$; basic bismuth benzoate $C_6H_5CO_2Bi(OH)_2$; bismuthyl salicylate $C_6H_4CO2(BiO)(OH)$; bismuth oxalate $(C_2O_4)_3Bi_2$; bismuth tartrate $Bi_2(C_4H_4O_6)_3,6H_2O$; bismuth lactate $(C_6H_9O_5)OBi,7H_2O$; bismuth citrate $C_6H_5O_7Bi$;

phenates: basic bismuth gallate $C_7H_7O_7Bi$; basic bismuth pyrogallate $C_6H_3(OH)_2(OBi)(OH)$.

Other inorganic or organic compounds are also suitable: bismuth phosphide BiP; bismuth arsenide $Bi_3As_4$; sodium bismuthate $NaBiO_3$; bismuth-thiocyanic acids $H_2[Bi(BNS)_5],H_3[Bi(CNS)_6]$ and their sodium and potassium salts; trimethylbismuthine $Bi(CH_3)_3$, triphenylbismuthine $Bi(C_6H_5)_3$.

Preferred bismuth derivatives for use in the process of the invention are: bismuth oxides; bismuth hydroxides; bismuth or bismuthyl salts of inorganic hydracids; bismuth or bismuthyl salts of inorganic oxyacids; bismuth or bismuthyl salts of aliphatic or aromatic organic acids; and bismuth or bismuthyl phenates.

A particularly suitable group of activators for carrying out the process of the invention is constituted by bismuth oxides $Bi_2O_3$ and $Bi_2O_4$; bismuth hydroxide $Bi(OH)_3$; neutral bismuth sulphate $Bi_2(SO_4)_3$; bismuth chloride $BiCl_3$; bismuth bromide $BiBr_3$; bismuth iodide $BiI_3$; neutral bismuth nitrate $Bi(NO_3)_3,5H_2O$; bismuthyl nitrate $BiO(NO_3)$; bismuthyl carbonate $(BiO)_2CO_3,0.5H_2O$; bismuth acetate $Bi(C_2H_3O_2)_3$; and bismuthyl salicylate $C_6H_4CO_2(BiO)(OH)$.

The quantity of activator used, expressed as the quantity of metal contained in the activator with respect to the weight of metal M used, can vary between wide limits. As an example, this quantity can be as low as 0.1% and can attain the weight of metal M used, or even exceed it without problems.

More particularly, this quantity is selected so that it provides the oxidation medium with 10 ppm to 900 ppm by weight of activator metal with respect to the hydroxyalkylated aromatic ether. In this respect, higher quantities of the order of 900 ppm to 1500 ppm can naturally be used, but with no great additional advantage.

The concentration by weight of hydroxyalkylated aromatic ether in the liquid phase is normally in the range 1% to 60%, preferably in the range 2% to 30%.

In practice, one manner of carrying out the process consists of bringing the solution comprising the hydroxyalkylated aromatic ether, any alkaline agent, the catalyst based on metal M, and any activator in the proportions indicated above into contact with molecular oxygen or a gas containing molecular oxygen.

Atmospheric pressure is used, but if necessary a pressure of 1 to 20 bar can be used.

The mixture is then stirred at the desired temperature until a quantity of oxygen corresponding to that necessary to transform the alcohol function into the aldehyde or ketone function has been consumed.

The reaction temperature depends on the thermal stability of the products to be prepared.

In accordance with the invention, the temperature is preferably selected so as to be within a range of 50° C. to 100° C., more preferably between 60° C. and 80° C.

At the end of the reaction, which preferably lasts 30 minutes to 4 hours, the aromatic ether carrying an oxidised group is recovered.

After cooling if necessary, the catalytic mass is separated from the reaction mass, for example by filtering.

The aldehyde or aromatic ketone obtained is recovered using conventional separation techniques, preferably by distillation or crystallisation.

As mentioned above, the process of the invention is particularly suitable for the preparation of vanillin and ethylvanillin.

The following examples illustrate the invention without in any way limiting its scope.

The terms conversion and selectivity mean the following:

$$\text{Degree of conversion} = \frac{\text{number of moles of ether transformed}}{\text{number of moles of ether introduced}}\%$$

$$\text{Selectivity} = \frac{\text{number of moles of hydroxyalkylated ether formed}}{\text{number of moles of ether transformed}}\%$$

EXAMPLE 1

0.5 g of an H-mordenite zeolite with a Si/Al molar ratio Si/Al of 18 and 12 ml of an aqueous formaldehyde solution (37% by weight, 160 mmole) were charged into a three-necked 50 ml reactor provided with a mechanical stirrer, an upflow cooling apparatus and a sample extraction system.

The reaction mixture was heated to 65° C. using a thermostatted bath and stirred at 500 rpm.

When the system was in thermal equilibrium, 1 ml of guaiacol (9 mmole) was introduced.

Samples were taken periodically and analysed by high performance liquid chromatography.

After 1 hour and 2 hours of reaction, the following performances were obtained:

| 1 hour | 2 hours |
|---|---|
| Conversion/guaiacol = 18% | Conversion/guaiacol = 32% |
| Selectivity/p-vanillol = 68% | Selectivity/p-vanillol = 62% |
| Selectivity/o-vanillol = 14% | Selectivity/o-vanillol = 13% |

EXAMPLES 2 TO 5

The above example was repeated using the same catalyst, varying either the temperature or the quantity of catalyst.

The reaction medium was analysed after different times and the results are shown in the following table:

TABLE I

| Ex | Temperature (°C.) | Quantity of catalyst (g) | Conversion/ guaiacol (%) | Selectivity/ p-vanillol (%) | Selectivity/ o-vanillol (%) | Time (min) |
|---|---|---|---|---|---|---|
| 2 | 85 | 0.5 | 32 | 48 | 10 | 30 |
|   |    |     | 49 | 58 | 11 | 60 |
|   |    |     | 73 | 49 | 11 | 120 |
| 3 | 85 | 0.25 | 23 | 34 | 7 | 30 |
|   |    |     | 32 | 38 | 8 | 60 |
|   |    |     | 47 | 43 | 10 | 120 |
| 4 | 65 | 0.75 | 19 | 59 | 11 | 30 |
|   |    |     | 42 | 56 | 13 | 60 |
|   |    |     | 50 | 55 | 11 | 120 |
| 5 | 50 | 0.5 | 9 | 53 | 9 | 120 |

EXAMPLES 6 TO 11

The operating procedure described for Example 1 was reproduced using 0.25 g of zeolites with different structures and Si/Al molar ratios and at a temperature of 85° C. The results are shown in the following table:

TABLE II

| Ex | Zeolite | Si/Al molar ratio | Time (min) | Conversion/ guaiacol (%) | Selectivity/ p-vanillol (%) | Selectivity/ o-vanillol (%) |
|---|---|---|---|---|---|---|
| 6 | H-mordenite | 10 | 120 | 12 | 24 | 5 |
| 7 | H-mordenite | 15 | 30 | 12 | 41 | 8 |
|  |  |  | 60 | 19 | 47 | 9 |
|  |  |  | 120 | 28 | 53 | 11 |
| 8 | H-mordenite | 49 | 30 | 10 | 36 | 10 |
|  |  |  | 60 | 19 | 37 | 9 |
|  |  |  | 120 | 34 | 29 | 8 |
| 9 | H-mordenite | 108 | 30 | 53 | 28 | 5 |
|  |  |  | 60 | 74 | 25 | 5 |
|  |  |  | 120 | 86 | 22 | 7 |
| 10 | H-β | 12.5 | 30 | 22 | 15 | 7 |
|  |  |  | 60 | 30 | 16 | 8 |
|  |  |  | 120 | 44 | 23 | 8 |
| 11 | H-β | 43 | 30 | 37 | 35 | 9 |
|  |  |  | 60 | 50 | 30 | 7 |
|  |  |  | 120 | 58 | 25 | 7 |

EXAMPLES 12 TO 15

Example 1 was reproduced using 0.25 g of H-mordenite zeolite with a Si/Al molar ratio of 100 at 85° C., varying the quantity and concentration of formaldehyde.

The reaction medium was analysed after different times. The results are shown in the following table:

TABLE III

| Ex | HCHO (mmole) | $C_{guaiacol}$ (mol/l) | Time (min) | Conversion/ guaiacol (%) | Selectivity/ p-vanillol (%) | Selectivity/ o-vanillol (%) |
|---|---|---|---|---|---|---|
| 12 | 80 | 0.7 | 30 | 54 | 9 | 6 |
|  |  |  | 60 | 74 | 6 | 4 |
|  |  |  | 120 | 77 | 7 | 5 |
| 13 | 160 | 0.7 | 30 | 42 | 28 | 7 |
|  |  |  | 60 | 59 | 29 | 7 |
|  |  |  | 120 | 68 | 35 | 9 |
| 14 | 240 | 0.45 | 30 | 32 | 38 | 9 |
|  |  |  | 60 | 54 | 36 | 8 |
|  |  |  | 120 | 67 | 31 | 7 |
| 15 | 80 | 1.2 | 30 | 43 | 17 | 4 |
|  |  |  | 60 | 62 | 17 | 6 |
|  |  |  | 120 | 76 | 22 | 3 |

EXAMPLE 16

Example 1 was reproduced using anisole in place of guaiacol.

0.75 g of H-mordenite zeolite with a Si/Al molar ratio of 18, 1 ml of anisole and 12 ml of an aqueous formaldehyde solution (37% by weight, 160 mmole) were used.

The reaction mixture was heated to 65° C. with stirring.

After 4 hours of reaction, the following performances were obtained:
Conversion/anisole=89%
Selectivity/p-hydroxymethylanisole=45%
Selectivity/o-hydroxymethylanisole=5%.

EXAMPLE 17

This example illustrates the preparation of vanillin from p-vanillic alcohol obtained from Example 1.

31 g of p-vanillic alcohol obtained from Example 1, 250 g of water and 0.2 mole of caustic soda in an aqueous 4N solution were introduced into a glass reactor provided with baffles.

3 g of a catalyst based on 2% of platinum deposited on carbon and 10 mg of bismuth sulphate were added.

The reactor was purged with oxygen and connected to an oxygen supply, establishing a slight pressure.

The reaction mixture was heated to 45° C. and stirred at 1000 rpm.

The medium was stirred at this temperature until the volume of oxygen corresponded to the theoretical quantity required to transform the alcohol to the aldehyde.

The operation was stopped and the reactor was purged with nitrogen.

The medium was acidified with an aqueous hydrochloric acid solution to a pH of 6.

The vanillin obtained was extracted 4 times with toluene.

Measurements using high performance liquid chromatography showed a 100% degree of conversion and a vanillin yield (number of moles of vanillin formed/number of moles of p-vanillic alcohol used) of 92%.

What is claimed is:

1. A process for the hydroxyalkylation of a carbocyclic aromatic ether consisting of reacting said aromatic ether with a carbonyl compound in the presence of a catalyst, wherein the hydroxyalkylation reaction is carried out in the presence of a catalytically effective quantity of a zeolite and at a temperature of no more than 100° C.

2. A process according to claim 1, wherein the carbocyclic aromatic ether has general formula (I):

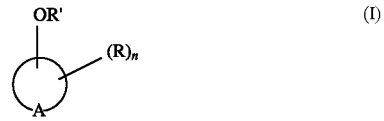

wherein:
A represents the residue of a cycle forming all or a portion of a monocyclic or polycyclic aromatic carbocyclic system containing at least one OR' group, the cyclic residue optionally carrying one or more substituents;
R represents one or more substituents which may be identical or different;
R' represents a hydrocarbon radical containing 1 to 24 carbon atoms;
R' and R optionally forming a cycle optionally containing a further heteroatom; and
n is a number less than or equal to 4.

3. A process according to claim 2, wherein R' is selected from the group consisting of:
a saturated or unsaturated, linear or branched acyclic aliphatic radical, containing 1 to 12 carbon atoms, the hydrocarbon chain optionally being interrupted by a heteroatom, a functional group or carrying a substituent;
a saturated or unsaturated, linear or branched acyclic aliphatic radical carrying a cyclic substituent optionally being substituted, said acyclic radical being bonded to the cycle by a valence bond, a heteroatom or a functional group;
a carbocyclic radical saturated or containing 1 or 2 unsaturations in the cycle, containing 3 to 8 carbon atoms in the cycle; said cycle optionally being substituted; and an aromatic carbocyclic radical, containing at least 4 carbon atoms, in the cycle; said cycle optionally being substituted.

4. A process according to claim 3, wherein R' represents a linear or branched alkyl radical containing 1 to 4 carbon atoms, or phenyl radical.

5. A process according to claim 2, wherein residue A represents the residue of a monocyclic aromatic carbocyclic compound containing at least 4 carbon atoms or the residue of a polycyclic carbocyclic compound, residue A optionally carrying one or more substituents on the aromatic nucleus.

6. A process according to claim 2, wherein the carbocyclic aromatic ether has formula (Ia):

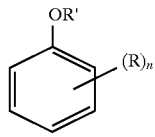
(Ia)

wherein:
n is a number less than or equal to 4;
radical R' represents a linear or branched alkyl radical containing 1 to 6 carbon atoms, or a phenyl radical;
radical(s) R is selected from the group consisting of:
a linear or branched alkyl radical containing 1 to 6 carbon atoms;
a linear or branched alkenyl radical containing 2 to 6 carbon atoms;
a cyclohexyl;
a benzyl radical;
a linear or branched alkoxy radical containing 1 to 6 carbon atoms;
an acyl group containing 2 to 6 carbon atoms; and
a radical with formula:
—$R_1$—OH
—$R_1$—$COOR_2$
—$R_1$—CHO
—$R_1$—$NO_2$
—$R_1$—CN
—$R_1$—N—$(R_2)_2$
—$R_1$—CO—N—$(R_2)_2$
—$R_1$—X or
—$R_1$—$CF_3$
wherein $R_1$ represents a valence bond or a saturated or unsaturated, linear or branched divalent, identical or different hydrocarbon radical containing 1 to 6 carbon atoms; radicals $R_2$, identical or different, represent a hydrogen atom or a linear or branched alkyl radical containing 1 to 6 carbon atoms; and X represents a halogen atom;
radicals R' and R and the 2 successive atoms of the benzene ring optionally forming between them a cycle containing 5 to 7 carbon atoms, optionally containing a further heteroatom.

7. A process according to claim 6, wherein n is equal to 0, 1 or 2.

8. A process according to claim 2, wherein n is greater than or equal to 1, radicals R' and R and the 2 successive atoms of the benzene ring being bonded together by an alkylene, alkenylene or alkenylidene radical containing 2 to 4 carbon atoms to form a saturated, unsaturated or aromatic heterocycle containing 5 to 7 carbon atoms in which one or more carbon atoms optionally being replaced by a heteroatom, the radicals OR' and R forming a dioxymethylene or dioxyethylene radical.

9. A process according to claim 6, wherein n equals 1, radical R' represents an alkyl radical containing 1 to 4 carbon atoms and R represents an alkoxy radical containing 1 to 4 carbon atoms or a hydroxy group.

10. A process according to claim 1, wherein the carbocyclic aromatic ether is anisole, phenetole, guaiacol, guetol, veratrol, 1,2-methylenedioxybenzene, or 2-methoxynaphthalene.

11. A process according to claim 7, wherein the carbonyl compound has formula (II):

wherein:
R3 and R4, identical or different, are selected from the group consisting of:
a hydrogen atom;
a linear or branched alkyl radical containing 1 to 6 carbon atoms;
a linear or branched alkenyl group containing 2 to 6 carbon atoms;
a phenyl group; and
an electron withdrawing group.

12. A process according to claim 11, wherein the electron withdrawing group is selected from the group consisting of:
a —CHO group;
a —$COOR_5$ group wherein $R_5$ represents a hydrogen atom or a linear or branched alkyl radical containing 1 to 6 carbon atoms;
a —$CX_2H$ group wherein X represents a halogen atom; and
a —CX3 group wherein X represents a halogen atom.

13. A process according to claim 11, wherein the carbonyl compound is selected from the group consisting of:
formaldehyde;
a formaldehyde generator;
trioxane;
linear polyformaldehydes having 8 to 100 ($CH_2O$) units;
glyoxylic acid;
chloral;
dichloroacetone;
acetaldehyde;
propionaldehyde;
dichloroacetaldehyde;
trichloroacetaldehyde;
methyl pyruvate; and
ethyl pyruvate.

14. A process according to claim 13, wherein the carbonyl compound is formaldehyde or a formaldehyde generator.

15. A process according to claim 1, wherein the zeolite is a natural or synthetic zeolite.

16. A process according to claim 15, wherein the zeolite is a natural zeolite selected from the group consisting of: chabazite, clinoptilolite, erionite, mordenite, phillipsite, and offretite.

17. A process according to claim 15, wherein the zeolite is a synthetic zeolite selected from the group consisting of:
synthetic zeolites with a one-dimensional network;
zeolites with a two-dimensional network; and
zeolites with a three-dimensional network.

18. A process according to claim 17, wherein the zeolite is a synthetic zeolite selected from the group consisting of ZSM-4 zeolite, L zeolite, ZSM-12 zeolite, ZSM-22 zeolite, ZSM-23 zeolite, ZSM-48 zeolite, mordenite, ferrierite; β zeolite, Y zeolite, X zeolite, ZSM-5 zeolite, ZSM-11 zeolite and offretite.

19. A process according to claim 18, wherein the zeolite is an H-β zeolite or an H-mordenite.

20. A process according to claim 1, wherein the hydroxyalkylation reaction is carried out in an aqueous medium or in the presence of an organic solvent selected from the group consisting of aliphatic hydrocarbons, aromatic hydrocarbons optionally being halogenated, aliphatic ether-oxides, cycloaliphatic ether-oxides, aromatic ether-oxides, polar aprotic solvents, nitrogen-containing compounds polar aprotic solvents, aliphatic nitrites, aromatic nitrites, tetramethylenesulphone, and dimethylsulphoxide.

21. A process according to claim 1, wherein the ratio between the number of moles of carbonyl compound and the number of moles of aromatic ether is between 1 and 50.

22. A process according to claim 1, wherein the ratio between the number of moles of carbonyl compound and the number of moles of aromatic ether is 8 to 25 when a synthetic zeolites selected from the group consisting of ZSM-4 zeolite, ZSM-5 zeolite, ZSM-11 zeolite, ZSM-12 zeolite, ZSM-22 zeolite, ZSM-23 zeolite, ZSM-48 zeolite, L zeolite, β zeolite and mordenites with a Si/Al molar ratio of 12 to 150, is used.

23. A process according to claim 1, wherein the quantity of catalyst is 5% to 80 by weight with respect to the aromatic ether used.

24. A process according to claim 11, comprising the following steps:
1) charging the catalyst, carbonyl compound with formula (II), and optionally an organic solvent;
2) charging the carbocyclic aromatic ether by introducing the same continuously or in fractions; and
3) heating the reaction mixture at a temperature of no more than 100° C.

25. A process according to claim 11, wherein the reaction is carried out continuously in a tube reactor comprising the solid catalyst disposed in a fixed bed.

26. A process according to claim 24, further comprising at the end of the hydroxyalkylation reaction the following steps:
4) recovering a liquid phase comprising the hydroxyalkylated aromatic ether;
5) extracting from an organic extraction solvent the organic phase obtained; and
6) directly oxidising said organic phase, or
7) counter-extracting with a basic aqueous solution said organic phase to obtain an aqueous phase containing the hydroxyalkylated product in salt form and oxidising the same.

27. A process according to claim 26, wherein the extraction solvent is selected from the group consisting of halogenated aliphatic hydrocarbons, aromatic hydrocarbons, halogenated aliphatic hydrocarbons, aromatic hydrocarbons, chloromethane, dichloromethane, 1,2-dichloroethane, chlorobenzene, dichlorobenzenes, trichlorobenzenes, butyl acetate, isopropyl acetate, amyl acetate, cyclohexyl acetate, ketones, acetone, methylethylketone, and methylisobutylketone.

28. A process according to claim 26, wherein the aqueous counter-extraction solution is an aqueous sodium or potassium hydroxide solution used is in the range 0.5 moles to 3 moles of sodium or potassium hydroxide with respect to the hydroxyalkylated aromatic ether to be oxidised.

29. A process for the oxidation of a hydroxyalkylated aromatic ether comprising oxidising the hydroxyalkylated aromatic ether in the liquid phase using molecular oxygen or a gas containing molecular oxygen in the presence of a catalyst based on a metal M selected from the metals in group 8 of the periodic classification, optionally further comprising, as activator, a metal.

30. A process according to claim 29, wherein the metal activator is nickel, cadmium, cerium, bismuth, lead, silver, tellurium or tin.

31. A process according to claim 29, wherein the catalyst is based on nickel, ruthenium, rhodium, palladium, osmium, iridium, or platinum or mixtures thereof.

32. A process according to claim 31, wherein the platinum catalyst is in the form of platinum black, platinum oxide, or the metal itself deposited on supports selected from the group consisting of carbon black, calcium carbonate, aluminas and activated silicas.

33. A process according to claim 29, wherein the quantity of catalyst to be used, expressed as the weight of metal M with respect to that of the hydroxyalkylated aromatic ether, is between 0.01 and 4%.

34. A process according to claim 29, wherein the activator is an organic or inorganic derivative of bismuth selected from the group consisting of bismuth oxides; bismuth hydroxides; bismuth salts of inorganic hydracids; bismuthyl salts of inorganic hydracids; bismuth salts of inorganic oxyacids; bismuthyl salts of inorganic oxyacids; bismuth salts of aliphatic or aromatic organic acids; bismuthyl salts of aliphatic or aromatic organic acids; bismuth phenates; and bismuthyl phenates.

35. A process according to claim 34, wherein the bismuth derivative is selected from the group consisting of bismuth oxides $Bi_2O_3$ and $Bi_2O_4$; bismuth hydroxide $Bi(OH)_3$; bismuth chloride $BiCl_3$; bismuth bromide $BiBr_3$; bismuth iodide $BiI_3$; neutral bismuth sulphate $Bi_2(SO_4)_3$; neutral bismuth nitrate $Bi(NO_3)_3,5H_2O$; bismuthyl nitrate $BiO(NO_3)$; bismuthyl carbonate $(BiO)_2CO_3,0.5H_2O$; bismuth acetate $Bi(C_2H_3O_2)_3$ and bismuth salicylate $C_6H_4CO_2(BiO)OH$.

36. A process according to claim 29, wherein the quantity of activator is selected so that the medium contains at least 0.1% by weight of metal activator with respect to the weight of metal M used, and 10 to 900 ppm by weight of metal M with respect to the hydroxyalkylated aromatic ether.

37. A process according to claim 29, wherein the oxidation reaction is carried out within a temperature range of 50° C. to 100° C.

38. A process for the preparation of vanillin by oxidation of 3-methoxy-4-hydroxybenzyl alcohol, wherein the 3-methoxy-4-hydroxybenzyl alcohol is obtained by hydroxymethylation of guaiacol carried out in the presence of an effective quantity of a zeolite using the process according to claim 1.

39. A process for the preparation of ethylvanillin by oxidation of 3-ethoxy-4-hydroxybenzyl alcohol, wherein the 3-ethoxy-4-hydroxybenzyl alcohol is obtained by hydroxymethylation of guetol carried out in the presence of an effective quantity of a zeolite using the process according to claim 1.

* * * * *